March 13, 1951 F. H. AXELL Plant Pat. 1,007
ROSE PLANT
Filed Oct. 14, 1947
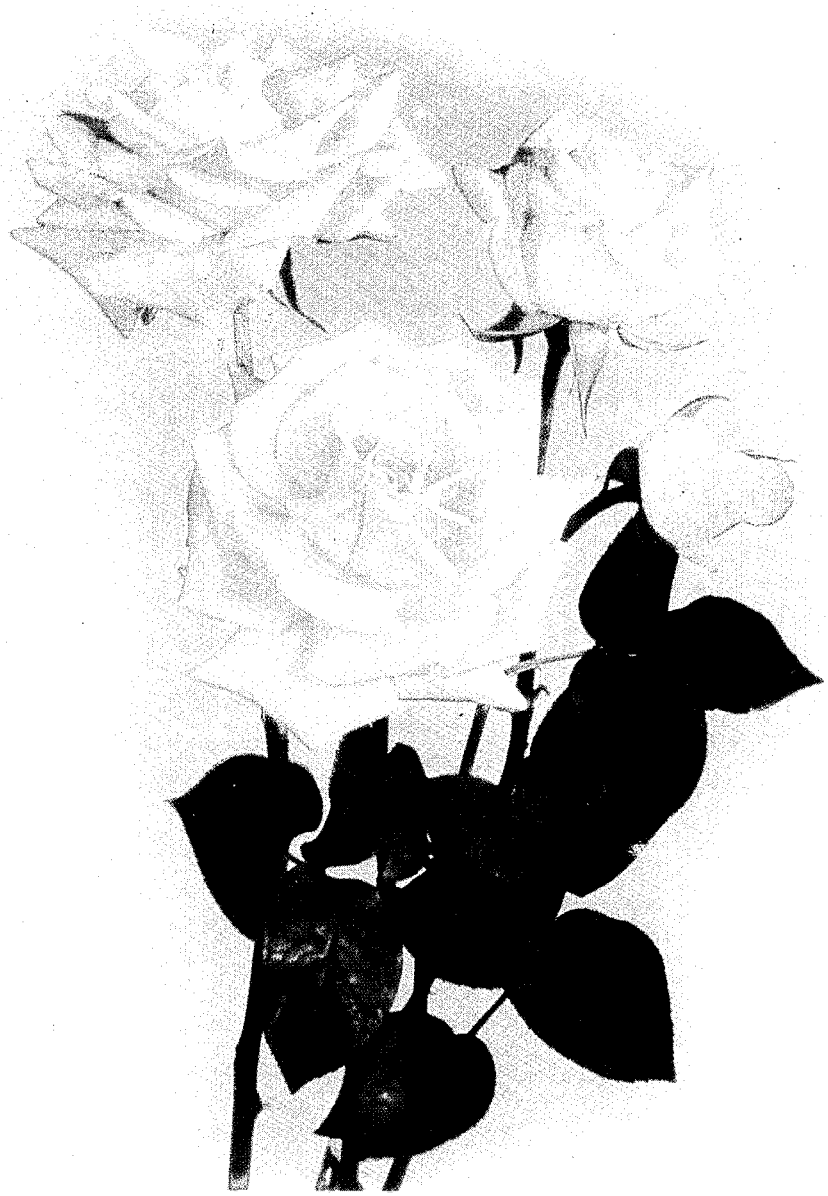
INVENTOR
FREDERICK H AXELL
BY Charles M. Fryer
ATTORNEY Patented Mar. 13, 1951

Plant Pat. 1,007

UNITED STATES PATENT OFFICE 1,007

ROSE PLANT

Frederick H. Axell, Mountain View, Calif., assignor to J. A. Axell & Company, San Francisco, Calif., a partnership Application October 14, 1947, Serial No. 779,783

1 Claim. (Cl. 47—61)

This invention relates to a new rose plant variety particularly adapted for greenhouse forcing to supply blooms to the cut-flower trade. The novel characteristics of this rose include a new and pleasing color.

This new rose is a sport of a rose known as "Pink Delight," an unpatented hybrid tea rose believed to be of European origin, commonly grown in greenhouses and furnishing blooms used by florists throughout the United States. Such parent rose is not the "Pink Delight" polyantha, a single petalled variety brought out by Laxton in 1922, and all references hereinafter to "Pink Delight" mean only the hybrid tea greenhouse rose bearing such name. Both the new rose and its parent rose have extreme usefulness in that they permit the continuous supply of blooms to florists during a period between September and July 1 of each season, when blooms on garden roses are scarce in many parts of the country.

A feature of importance of this sport of "Pink Delight" is its soft pink self-color markedly distinguishing it from the deeper, purplish pink of "Pink Delight." This color lends the new rose to a range of florist uses for which "Pink Delight" would not be acceptable. Thus the color of "Pink Delight" in bud form is slightly deeper than Rose color as shown by Plate XII of Ridgway's "Color Standards and Nomenclature," whereas the bud of the new rose is Thulite Pink (Plate XXVI). The open flower of "Pink Delight" is approximately Mallow Purple (Plate XII), whereas the new rose in open flower is slightly lighter than Deep Rose Pink (Plate XII). However, the new rose includes the other good features which make its parent, "Pink Delight," valuable for supplying the florist trade, such as good growth characteristics, free habit of bloom, and long lasting qualities of bloom.

The new rose has been asexually reproduced and its distinctive characteristics have come true to form in the reproductions.

The accompanying illustration shows four blooms of the new rose, including a bud, a partially opened flower and a fully opened flower. Since the illustration cannot well depict the exact, pleasing coloring of the natural blooms, reference is made to the description herein where the colors are specifically set forth.

The following is a detailed description of the new rose; and the colors designated were taken from Ridgway's "Color Standards and Nomenclature":

*General information*

Type: Bush plant particularly adapted for greenhouse growing to supply flowers for the cut-flower trade.

Class: Hybrid tea.

Breeding or discovery: By Frederick H. Axell at Sunnyvale, California.

*Sport.*—Of an unpatented rose known as "Pink Delight" and discovered in 1944 in the greenhouse planting of "Pink Delight" stock.

*Propagation.*—By budding, conducted at Sunnyvale, California, by Frederick H. Axell. The variety has retained its distinguishing characteristics through succeeding propagations.

*Flower*

Locality where grown: Sunnyvale, California.

Flowers borne: Singly to the stem and on strong, long stems.

Quantity of bloom: Abundant under greenhouse conditions.

Continuity: Continuous.

Fragrance: Moderate tea.

Bud: Long peduncle. Bud is slender, erect, light green with few green prickles.

Before calyx breaks, bud is small, globular, with a conspicuous neck, with foliaceous appendages on the surface of the bud, such foliaceous parts extending beyond the tip of the bud equal to one-quarter of its length.

As calyx breaks, the color is slightly deeper than Rose color (Plate XII).

As first petal opens its size is medium and its form is long and ovoid; the outside color is Thulite Pink (Plate XXVI) and the inside color is Rose color (Plate XII). It opens up well.

Bloom: The size when fully open is four to four and one-half inches. Petalage is very double with from thirty-six to forty-five petals arranged regularly, usually with no stamens showing. The form is cupped, with a high center, becoming flat, with the petals remaining at first loosely flat, cupped and rolled outward, and becoming later, at maturity, loosely rolled outward.

Petals: Thick, leathery, with inside velvety and outside satiny.

*Shape.*—Outside petals are round, with one notch, and intermediate petals are round.

*Color.*—The colors are modified only by a small blaze of Lemon Yellow (Plate IV) at the base of the inside surface of each petal, this blaze of color shading into a narrow margin of white, but these colors are barely discernible unless the petals are removed from the flower. The colors both in the newly opened flower and a flower open for three days, grown in a greenhouse, are as follows: Outside petal—outside surface: Thulite Pink (Plate XXVI); inside surface: Deep Rose Pink (Plate XII). Intermediate and inner petals—outside surface: Deep Rose Pink (Plate XII); inside surface: Rose Color (Plate XII).

The general color effect is Deep Rose Pink (Plate XII) in the newly opened flower, with the color only a shade lighter after the flower is open three days.

Behavior: Petals hang on for life of bloom and then drop off cleanly.

Flower longevity: 5 days on bush under greenhouse conditions; cut flowers kept at living room temperature 4 days.

Quantity of bloom: Approximately thirty blooms per plant a season for cutting purposes.

Time of bloom: In greenhouse the peak bloom occurs between September and July 1 of each season, but flowers are available continuously.

*Reproductive organs*

Stamens: Few, arranged irregularly, mixed with petaloids.

Filaments: Medium, pinkish, with anthers.

Anthers: Medium, reddish brown, open at various times.

Pollen: Moderate, yellow.

Pistils: Many.

Styles: Uneven, short, thin and bunched.

Stigma: Yellow red.

Ovaries: All enclosed in calyx.

Hips: Very globular, green, very smooth and with thin walls.

Sepals: Long and spear shaped.

*Plant*

Foliage:

*Leaves.*—Compound of five with many leaflets, and leaves very abundant, heavy and leathery.

*Leaflets.*—Lanceolate and linear.

*Color.*—In both mature and young foliage, the upper surface is dark green, the under surface, green.

*Rachis.*—Upper side: smooth. Under side: thorny.

*Disease.*—Resistant under greenhouse conditions where rose is generally grown.

Growth:

*Habit.*—Upright, much branched.

*Growth.*—Vigorous.

*Canes.*—Medium.

*Main stems.*—Brown. *Thorns*—several, hooked downward with narrow base. *Prickles*—few, bronze red. *Hairs*—none.

*Branches and new shoots.*—Green, bronze. *Thorns*—several, long and straight with narrow base. *Prickles*—few. *Hairs*—none.

Having thus described my rose, I claim:

A new and distinct variety of rose plant, retaining the characteristics of growth, free habit of bloom, and long lasting qualities of bloom making its parent variety suitable for greenhouse forcing to supply blooms to the cut-flower trade, and characterized as to novelty by differing from such parent variety in the unique color of its flowers substantially as shown and described.

FREDERICK H. AXELL.

No references cited.